United States Patent [19]

Kim et al.

[11] Patent Number: 5,304,475
[45] Date of Patent: Apr. 19, 1994

[54] METHOD FOR PRODUCTION OF L-PHENYLALANINE BY RECOMBINANT E. COLI

[75] Inventors: Hwa Y. Kim; Hong Rhym; Dong J. Lee; Chan H. Won; Byung L. Lim; Hong G. Choi, all of Seoul, Rep. of Korea

[73] Assignee: Miwon Co., Ltd., Dobong-ku, Rep. of Korea

[21] Appl. No.: 851,682

[22] Filed: Mar. 12, 1992

[30] Foreign Application Priority Data

Sep. 12, 1991 [KR] Rep. of Korea ............... 91-15909

[51] Int. Cl.$^5$ .................... C12P 15/22; C12N 15/73; C12N 1/21
[52] U.S. Cl. .................... 435/108; 435/69.1; 435/71.2; 435/252.3; 435/252.33; 435/172.3; 435/320.1; 435/849; 536/23.2; 935/14; 935/29; 935/41; 935/43; 935/56; 935/60; 935/61; 935/73
[58] Field of Search .............. 435/69.1, 71.2, 108, 435/252.3, 252.33, 172.3, 320.1, 849; 935/14, 29, 41, 43, 56, 73, 60, 61

[56] References Cited

U.S. PATENT DOCUMENTS 5,008,190  4/1991  Lee et al. ..................... 435/108
5,030,567  7/1991  Lee et al. ..................... 435/108

FOREIGN PATENT DOCUMENTS 60-160890  8/1985  Japan.
89-3680  9/1989  Rep. of Korea.
89-3681  9/1989  Rep. of Korea.
89-3682  9/1989  Rep. of Korea.
89-3714  9/1989  Rep. of Korea.

OTHER PUBLICATIONS

Sugimoto, S. et al. "Hyperproduction of Phenylalanine by *Escherichia coli*: Application of a Temperature-Controllable Expression Vector Carrying the Repressor-Promoter System of Bacteriophage lambda" J. Biotechnology 5:237–253 (1987).

*Primary Examiner*—Robert A. Wax
*Assistant Examiner*—Rebecca Prouty
*Attorney, Agent, or Firm*—Birch, Stewart, Kolasch & Birch

[57] ABSTRACT

A novel *E. coli* (KCCM 10,013) which can produce high yields of L-phenylalanine and a method for production of L-phenylalanine by recombinant *E. coli* which may be transformed with a novel plasmid pMW16 containing two promoters and a temperature-sensitive repressor for expressing a pheA gene and an aroF gene wherein chorismate mutase p-prephenate dehydratase is coded for by the pheA gene and 3-deoxy-D-arabinoheptulosonate.7-phosphate synthase is coded for by the aroF gene.

7 Claims, 2 Drawing Sheets

METHOD FOR PRODUCTION OF L-PHENYLALANINE BY RECOMBINANT E. COLI

BACKGROUND OF THE INVENTION

1. Field of the Invention

The present invention relates to a method for production of L-phenylalanine by recombinant *Escherichia coli* (hereinafter "*E. coli*"). More particularly, the present invention relates to a novel *E. coli* containing a plasmid for the production of L-phenylalanine and a process for the production of L-phenylalanine by use of the novel microbe.

2. Description of the Prior Art

L-phenylalanine is a kind of essential amino acid and can be used for the synthetic production of ASPARTAME ®, a sweetening agent. There are many known methods for production of L-phenylalanine by use of microbes. For example, Japanese Patent Laid-Open No. 60-160,890 discloses a method for production of L-phenylalanine by use of Brevibacterium or Corynebacterium sp. which require tyrosine. Japanese Patent Laid-Open No. 55-165,797 discloses a similar method by use of *E. coli* which requires tyrosine and which is resistant to tryptophane analogues. Korean Patent Publication Nos. 89-3680 and 89-3681 disclose a similar method by use of an *E. coli* strain which is revertant from tyrosine and tryptophan auxotrophy and is resistant to phenylalanine, tyrosine and tryptophan analogues. Korean Patent Publication Nos. 89-3,682 and 89-3,714 disclose methods for production of phenylalanine by recombinant *E. coli* using amplication of the copy number of a gene which codes for a rate-limiting enzyme.

SUMMARY OF THE INVENTION

Accordingly, it is an object of the present invention to provide a novel *E. coli* (KCCM 10,013) which can produce high yields of L-phenylalanine.

Another object of the present invention is to provide a method for production of L-phenylalanine by recombinant *E. coli* which may be transformed with a novel plasmid pMW16 containing two promoters and temperature-sensitive repressor for expressing a pheA gene and an aroF gene. Chorismate mutase p-prephenate dehydratase is coded for by the pheA gene and 3-deoxy-D-arabinoheptulosonate.7-phosphate synthase is coded for by the aroF gene.

A further object of the present invention is to provide a replicable recombinant plasmid pMW16 which is capable of transforming an *E. coli* to produce a transformed *E. coli* exhibiting a high level of phenylalanine production.

Still another object of the present invention is to provide a method for the production of phenylalanine in high yield, which comprises cultivating the *E. coli* of the present invention in a culture medium.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION

The aroF and pheA genes for use in L-phenylalanine production are derived from *E. coli* MWPWJ 304 (KCCM 10,013).

Figure 1:
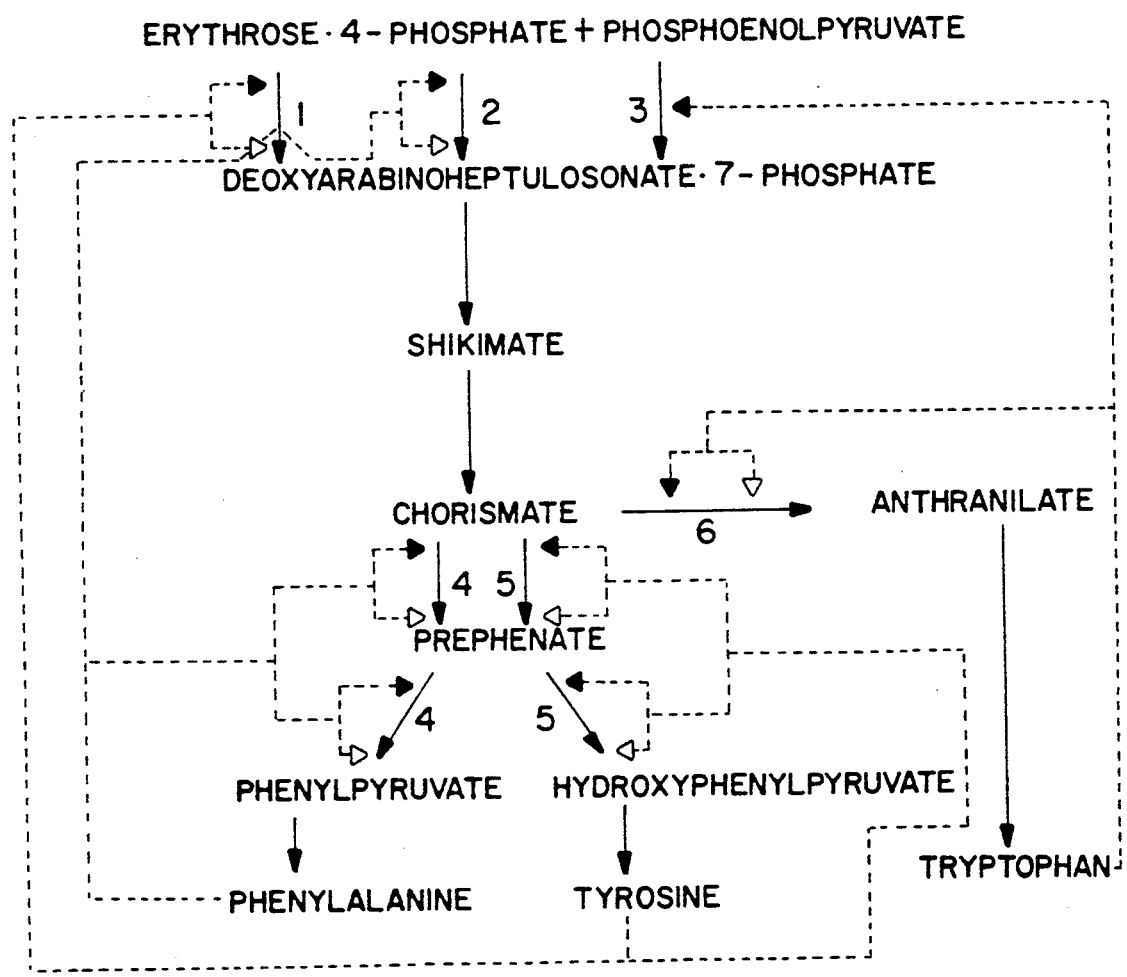
FIG. 1 illustrates the metabolic pathways for biosynthesis of aromatic amino acids in *E. coli*.

Referring now in detail to the drawings for the purpose of illustrating the present invention, as shown in FIG. 1, the process for preparing L-phenylalanine by use of the recombinant plasmid is controlled by enzyme action in *E. coli* cells. One of the enzymes which controls the reaction is chorismate mutase P-prephenate dehydratase. Another of the enzymes which controls the reaction is the enzyme, 3-deoxy-D-arabino-heptulosonate.7-phosphate synthase (hereinafter "DAHP synthase"). The DAHP synthase exists as three isoenzymes which are encoded for by the aroF, aroG and aroH genes, respectively. In the present invention, in order to greatly increase the expression of the pheA and aroF genes, a $P_L$ promotor of λ phage is connected to each gene and a temperature-sensitive repressor is used to control the expression of the gene.

Figure 2:
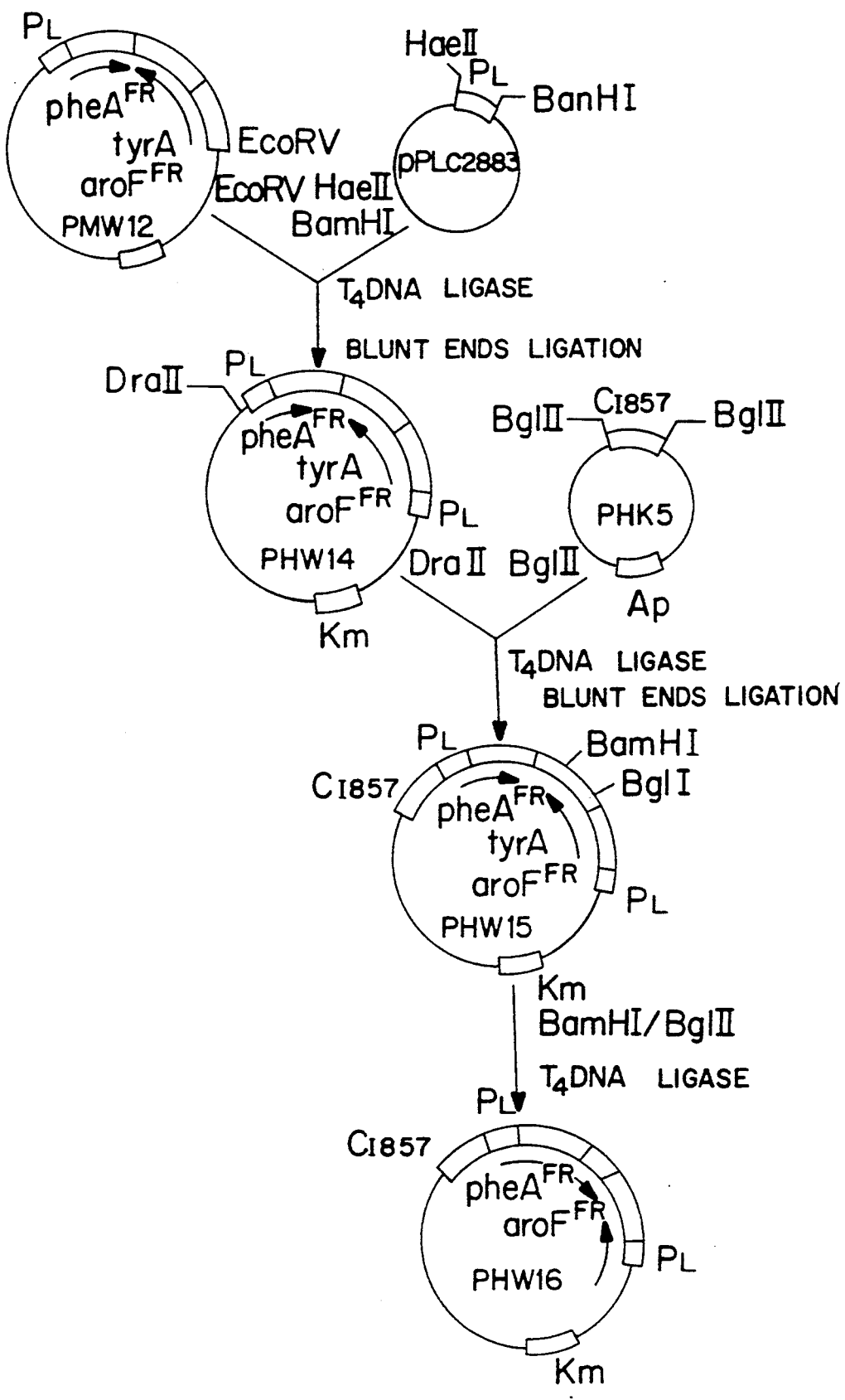
FIG. 2 illustrates steps for preparing a recombinant plasmid pMW16 and its restriction map.

As shown in FIG. 2, the method for preparing the plasmid pMW16 is described in Recombinant DNA Methodology and Molecular Cloning. The process for the preparation of the recombinant plasmid pMW16 is described in Molecular Cloning, A Laboratory Manual (T. Mariatis et al.) and Current Protocols in Molecular Biology (Frederick M. Ausubel et al.).

Accordingly, a novel strain MWPWJ 304 for use in manufacturing the L-phenylalanine is obtained. The novel strain MWPWJ 304 was deposited at the Korean Fermentation Culture Collection on Aug. 30, 1991 in accordance with the conditions of the Budapest Treaty and was assigned deposit number KCCM 10,013.

The present invention will now be described in more detail in connection with the following examples which should be considered as being exemplary and not limiting of the invention.

EXAMPLE 1

Preparation of Plasmid pMW16

(1) Isolation of pMW12 DNA pMW12 (U.S. Pat. Nos. 5,008,190 and 5,030,567), a recombinant plasmid containing the pheA gene and the aroF gene is digested with EcoRV in medium salt restriction enzyme buffer (50 mM of sodium chloride, 10 mM of tris-HCl (pH 7.5), 10 mM of magnesium chloride, and 1 mM of dithiothreitol) at 37° C. for 16 hours. The digested DNA is treated with a phenol-chloroform mixture and precipitated by ethanol to produce linearized plasmid DNA. This plasmid DNA is treated with calf intestinal alkaline phosphatase (hereinafter "CIP") to prevent the linearized plasmid DNA from self-ligating.

(2) isolation of $P_L$ promoter fragment

The plasmid pPL$_C$ 2833 is digested by the restriction enzyme Hae II and Bam HI andea 0.26 Kb DNA fragment containing the P$_L$ promoter, is recovered from an agarose gel having a low-melting point and the DNA is purified from it. The 0.26 kb P$_L$ fragment having a cohesive end is treated with T$_4$ DNA polymerase in reaction enzyme buffer (50 mM of Tris-HCl (pH 8.0), 5 mM of magnesium chloride, 5 mM of dithiothreitol, 50 μg/ml of bovine serum albumin (BSA), 100 μM of dATP, 100 μM of dGTp, 100 μM dCTP, and 100 μM dTTp) at a temperature of 11° C. for 20 minutes to form blunt ends.

(3) preparation of Plasmid pMW14

The phosphatase-treated, linearized plasmid pMW12 of the above-mentioned step (1) is mixed with the P$_L$ promoter fragment having the blunt ends at both ends obtained from the above-mentioned step (2) in an amount 1:3 and treated with T$_4$ DNA ligase at a temperature of 16° C. for 16 hours so as to ligate the fragments. The combined recombinant plasmid is transformed by a conventional calcium chloride method into *E. coli* MWEC203-7 which requires phenylalanine for growth. The transformed strain is cultivated in MM culture media containing 50 μg/ml of Kanamycin antibioti (10 g of glucose, 4 g of ammonium sulfate, 2 g of morobasic potassium phosphate, 1 mg of HCL, 0.5 g of fumaric acid, 20 g of agar, 1 l of distilled water,.and pH 7.4). The recombinant plasmid pMW14 is separated from the cultivated strain which grew on the MM culture media containing 50 μg/ml of Kanamycin.

(4) preparation of pMW15

Plasmid pMK5 containing a temperature-sensitive repressor CI$_{857}$ gene is treated with the restriction Bgl II and the 0.9 Kb DNA fragment is recovered from a 0.9% agarose gel and then treated with T$_4$ DNA polymerase to form the blunt ends. The plasmid pMW14 obtained from the above-mentioned step (3), which is combined with the P$_L$ promoter at the front of aroF gene is digested by Dra III and treated with CIP so as to remove the 5'-phosphate groups. Thereafter, the treated plasmid pMW14 is mixed with the CI$_{857}$ fragment having blunt ends at both ends and the two fragments are joined by T$_4$ DNA ligase. The recombinant plasmid is transformed into *E. coli* HB101 to produce pMW15.

(5) Preparation of pMW16

Isolated pMW15 recombinant plasmid is digested with Bam HI and Bgl II and treated with T$_4$ DNA ligase to produce pMW16. The pMW15 plasmid contains a whole tyrA gene. In pMW16, a 0.7 Kb fragment of the tyrA gene is removed therefrom. The pMW16 recombinant plasmid is transformed into a temperature-sensitive tyrosine-leaky strain, *E. coli* MWWJ 304 (KFCC 10737, deposited to Korean Fermentation Culture Collection, Aug. 30, 1991) and then is cultivated in culture media containing 50 μg/ml of Kanamycin at 37° C. for 24 hours. Among the strains transformed with pMW16, a strain optimally producing L-phenylalanine, MWPWJ 304 (KCCM 10,013, deposited to Korean Culture of Microorganisms, Jan. 28, 1992) was isolated. The biochemical properties of the novel strain MWPWJ 304 (KCCM 10,013) are the same as those of host strain MWWJ 304 (KFCC 10,737). However, the novel strain MWPWJ 304 requires more tyrosine for growth and producing L-phenylalanine when compared with the host strain MWWJ 304. Furthermore, the yield of L-phenylalanine and the activity of DAHP synthase of the novel strain MWPWJ 304 are increased.

Experimental Example 1

The enzyme activity and yield of L-phenylalanine of the novel strain MWPWJ 304 are increased when compared with the present strain as follows (Table I, Table II):

TABLE I

| Strain | Enzyme activity of DAHP synthase | |
|---|---|---|
| | cultivating temperature | enzyme activity units |
| MWPEC 13-60 (KCTC 8337P) | 32° C. | 1.0 |
| MWWJ 304 (KFCC 10,737) | 37° C. | 0.9 |
| MWPWJ 304 (KCCM 10,013) | 37° C. | 3.1 |

The above data was obtained by the method of I. Shiio et al (Journal of Biochemistry, 75, 987-997, 1974). The enzyme activity of MWPWJ 304 (KCCM 10,013) is stated relative to that of MWPEC 13-60 (KCTC 8337 P). The culture media of MWWJ 304 (KFCC 10,737) and MWPWJ 304 (KCCM 10,013) contained an additional 100 mg/l of L-tyrosine compared with that of MWPEC 13-60.

Example 2

Preparation of L-phenylalanine

TABLE II

| | Yield of L-Phenylalanine (g/l) | |
|---|---|---|
| | strain | |
| Culture temperature (°C.) | MWWJ 304 (KFCC 10,737) | MWPWJ 304 (KCCM 10,013) |
| 31 | 14.9 | 13.7 |
| 34 | 20.6 | 21.2 |
| 37 | 31.5 | 50.8 |
| 39 | 15.5 | 22.8 |

Only 200 mg/l of L-tyrosine was added to the fermentation media of MWWJ 304 (KFCC 10,737) and MWPWJ 304 (KCCM 10,013), respectively.

| (A) Strain | |
|---|---|
| MWPWJ 304 (KCCM 10,013) | |
| (B) Culture media | |
| Glucose | 3% |
| Tryptone | 1% |
| Bactoyeast extract | 1% |
| Sodium chloride | 0.1% |
| Kanamycin | 10 mg/l |
| pH | 7.0 |
| (C) Fermentation Media | |
| Glucose | 6% |
| Potassium sulfate | 0.04% |
| Ammonium sulfate | 2% |
| Sodium citrate | 0.05% |
| Fumaric acid | 0.05% |
| Magnesium chloride | 0.08% |
| Monobasic potassium phosphate | 0.1% |
| Diabasic potassium phosphate | 0.1% |
| Bactoyeast extract | 0.1% |
| Monosodium glutamate | 00.5% |
| Cobalt chloride | 0.1 mg/l |
| Zinc sulfate | 1 mg/l |
| Manganese chloride | 2 mg/l |
| Calcium chloride | 5 mg/l |
| Ferric chloride | 20 mg/l |
| L-tyrosine | 300 mg/l |
| Thiamine Hydrochloride | 10 mg/l |
| Nicotinic acid | 10 mg/l |
| pH | 7.0 |

(D) Fermentation Method 40 ml of the culture medium is charged into a 500 ml test flask and autoclaved at 120° C. for 20 minutes. After sterilizing, the novel *E. coli* strain MWPWJ 304 (KCCM 10,013) is inoculated into the flask and cultivated at 37° C. for 16 hours with shaking to provide inoculum. The fermentation medium is prepared using the above-mentioned formulation. After 3.5% calcium carbonate autoclaved separately is added to the fermentation medium and 2 ml of inoculum is added thereto, the fermentation medium is agitated and fermented at 37° C. for 36 hours. After completing the fermentation, the amount of L-phenylalanine accumulated is 16.2 g/l.

Example 3

Preparation of L-phenylalanine

The (A) Strain, (B) Culture Media, and (C) Fermentation Medium except for 400 mg/l of L-tyrosine, are the same as used in Examples 1 and 2.

(D) Fermentation Method 1 l of the fermentation medium is charged into a 2 l fermentor and autoclaved at 120° C. for 15 minutes. The novel strain MWPWJ 304 (KCCM 10,013) is added to the 50 ml of culture medium in a 500 ml flask and cultivated at 37° C. for 16 hours with shaking. 50 ml of the cultured broth is charged into the fermentor operating at 1,000 rpm and 1.0 vvm (oxygen rate) at 37° C. for 48 hours. During fermentation, a pH of 7.0 is maintained by adding ammonium hydroxide and a 60% glucose solution is added to the fermentor three times when the level of glucose drops below 1%.

The total amount of glucose which is used in the fermentation is 185 g/l. L-phenylalanine is obtained in a concentration of 50.8 g/l. 1 l of fermentation solution is purified by a conventional method such as absorbing with an ion-exchange resin and isolating with ammonium hydroxide to produce 45.7 g/l of L-phenylalanine as crude crystals.

Example 4

Example 3 was repeated except that 27 l of the culture is charged into a 50 l fermentation apparatus, and 1.3 l of the cultured broth is charged into the fermentation apparatus operating at 450 rpm and 1.0 vvm. The amount of L-phenylalanine produced is 49.1 g/l.

The invention being thus described, it will be obvious that it may be varied in many ways. Such variations are not to be regarded as a departure from the spirit and scope of the invention, and all such modifications as would be obvious to one skilled in the art are intended to be included in the scope of the following claims.

What is claimed is:

1. A replicable recombinant plasmid, comprising DNA encoding two promoters and a temperature-sensitive repressor for expressing a pheA$^{FR}$ gene which codes for chorismate mutase p-prephenate dehydratase and an aroP$^{FR}$ gene which codes for 3-deoxy-D-arabinoheptulosonate.7-phosphate synthase, said recombinant plasmid being plasmid pMW 16 contained in *E. coli* MWPWJ 304 (KCCM 10,013).

2. *E. coli* MWPWJ 304 (KCCM 10,013), which has an optimum L-phenylalanine production capability by virtue of containing pheA$^{FR}$ and aroF$^{FR}$ genes as elements of an extrachromosomal plasmid.

3. A process for production of phenylalanine, which comprises cultivating an *E. coli* strain which has the plasmid pMW 16, isolated from MWPWJ 304 (KCCM 10,013), in a culture medium.

4. The process for production of L-phenylalanine of claim 3, wherein said cultivating is conducted in the presence of a sugar.

5. The process for production of L-phenylalanine of claim 4, wherein said sugar is glucose.

6. The process for production of L-phenylalanine of claim 4, wherein said cultivating is conducted at a temperature of 37° C.

7. The process of claim 3, wherein said *E. coli* strain is *E. coli* MWPWJ 304 (KCCM 10,013).

* * * * *